United States Patent [19]

Wade

[11] Patent Number: 4,474,953
[45] Date of Patent: Oct. 2, 1984

[54] PROCESS AND INTERMEDIATES FOR THE PREPARATION OF 3(1H-TETRAZOL-5-YL)-4H-PYRIDO[1,2-A]PYRIMIDIN-4-ONES

[75] Inventor: James J. Wade, Oakdale, Minn.

[73] Assignee: Riker Laboratories, Inc., St. Paul, Minn.

[21] Appl. No.: 416,242

[22] Filed: Sep. 9, 1982

[51] Int. Cl.³ .................. C07D 471/04; C07D 401/12
[52] U.S. Cl. ..................................... 544/282; 546/276
[58] Field of Search ................. 544/282, 250; 542/424

[56] References Cited

U.S. PATENT DOCUMENTS

| | | | |
|---|---|---|---|
| 3,585,198 | 6/1971 | Meszaros et al. | 260/251 |
| 3,960,847 | 6/1976 | Yale | 544/282 |
| 4,122,274 | 10/1978 | Juby | 544/282 |
| 4,209,620 | 6/1980 | Juby | 544/252 |
| 4,223,031 | 9/1980 | Covington et al. | 424/251 |

FOREIGN PATENT DOCUMENTS 2519816  10/1976  Fed. Rep. of Germany ...... 544/282

OTHER PUBLICATIONS

Meszaros et al., Arzneim-Forsch. 22, 815–829 (1972).
Finnegan et al., J. Am. Chem. Soc., 80, 3908-3911 (1958).
Yevich et al., J. Med. Chem. 25, 864–868 (1982) (Jul. issue).

*Primary Examiner*—Paul M. Coughlan, Jr.
*Assistant Examiner*—Diana G. Rivers
*Attorney, Agent, or Firm*—Donald M. Sell; James A. Smith; Robert W. Sprague

[57] ABSTRACT

A process for preparing compounds of the formula

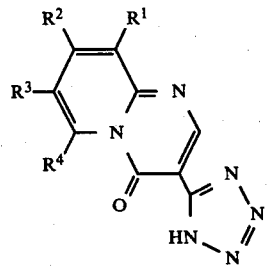

wherein $R^1$, $R^2$, $R^3$ and $R^4$ are independently selected from the group consisting of H, an alkyl group containing 1 to about 4 carbon atoms, an alkoxy group containing 1 to about 4 carbon atoms and halogen. The process involves reacting together a 2-aminopyridine, an alkyl tetrazol-5-ylacetate, and a trialkyl orthoformate and cyclizing the resulting intermediate.

5 Claims, No Drawings

PROCESS AND INTERMEDIATES FOR THE PREPARATION OF 3(1H-TETRAZOL-5-YL)-4H-PYRIDO[1,2-A]PYRIMIDIN-4-ONES

FIELD OF THE INVENTION

This invention relates to a novel synthetic process. More specifically, it relates to a process for the preparation of compounds containing a pyrimidinone ring, a pyridine ring fused to the pyrimidinone ring, and a tetrazole ring bonded to the pyrimidinone ring at a position alpha to the keto group thereof. Novel intermediates are also included within the scope of the invention.

BACKGROUND OF THE INVENTION

U.S. Pat. Nos. 4,122,274 and 4,209,620 describe the antiallergic agents 3-(1H-tetrazol-5-yl)-4H-pyrido[1,2-a]pyrimidin-4-ones and methods for their synthesis. Unfortunately, the methods disclosed therein are not particularly convenient since they generally require several steps and/or the use of complex procedures and/or dangerous reactants such as azides.

Ethyl tetrazol-5-ylacetate is described by Finnegan, et al., *J. Am. Chem. Soc.*, 80, 3908 (1958). It is used to prepare 5-phenyltetrazole and various other substituted tetrazoles.

DETAILED DESCRIPTION

The present invention relates to novel processes for preparing compounds of Formula I

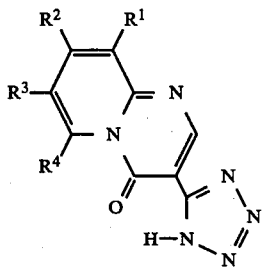

wherein $R^1$, $R^2$, $R^3$ and $R^4$ are independently selected from the group consisting of H, an alkyl group containing 1 to about 4 carbon atoms, an alkoxy group containing 1 to about 4 carbon atoms and halogen. The preferred halogen substituent is chlorine. Compounds of Formula I are useful antiallergic agents as indicated in said U.S. Pat. Nos. 4,122,274 and 4,209,620, both incorporated herein by reference.

One process of the present invention for the preparation of compounds of Formula I is illustrated in general terms as follows in Procedure A:

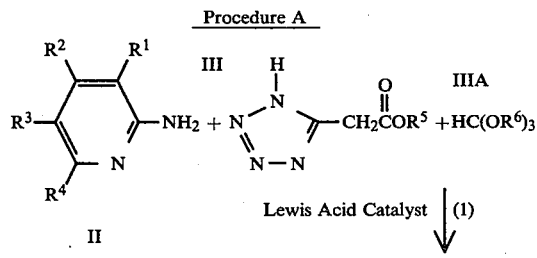

-continued
Procedure A

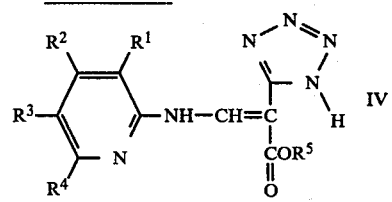

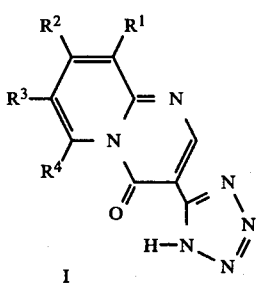

wherein $R^1$, $R^2$, $R^3$ and $R^4$ are as defined hereinabove; $R^5$ is an alkyl group containing 1 to about 4 carbon atoms; and each $R^6$ is independently an alkyl group containing 1 to about 4 carbon atoms. Compounds of Formula IV are the novel intermediates.

In step (1) of Procedure A, a 2-aminopyridine of Formula II, an alkyl tetrazol-5-ylacetate of Formula III, and a trialkyl orthoformate ester of Formula IIIA are reacted together in the presence of a Lewis acid catalyst. Useful 2-aminopyridines of Formula II are well known to the art. For example, useful 2-aminopyridines are described in the aforementioned U.S. Pat. No. 4,209,620. Specific examples of suitable 2-aminopyridines include 2-aminopyridine, 2-amino-5-bromopyridine, 2-amino-5-chloropyridine, 2-amino-3,5-dibromopyridine, 2-amino-3,5-dichloropyridine, 2-amino-4,6-dimethylpyridine, 2-amino-3-methoxypyridine, and 2-amino-6-methoxypyridine.

Ethyl tetrazol-5-ylacetate is the preferred alkyl tetrazol-5-ylacetate of Formula III. The ratio of alkyl tetrazol-5-ylacetate of Formula III to the 2-aminopyridine of Formula II is preferably about 1:1.

Examples of suitable trialkyl orthoformate esters of Formula IIIA for employment in step (1) are trimethyl orthoformate and triethyl orthoformate. At least one mole of trialkyl orthoformate per mole of alkyl tetrazol-5-ylacetate is required to obtain complete reaction. It is preferred that a slight molar excess of the trialkyl orthoformate ester be employed.

Examples of suitable Lewis acid catalysts for employment in step (1) are zinc chloride and stannous chloride. The preferred catalyst is aluminum trichloride. Weaker acids such as boron trifluoride and p-toluenesulfonic acid generally provide poorer yields in most cases and are not preferred. Catalytic amounts, e.g., less than 30 mole percent, and preferably about 10 mole percent of catalyst, are used.

The reaction of step (1) may be conducted by combining the reactants and heating at about 100° to 150° C. Any volatile distillates may be collected if desired. The reaction of step (1) may be carried out in an inert solvent such as dioxane or trichloroethylene. The novel intermediate of Formula IV may be isolated at this point and purified or the reaction product of step (1) may be used directly in step (2) without isolation and purification of the intermediate of Formula IV.

In step (2) the intermediate of Formula IV is preferably combined with polyphosphoric acid and heated to effect cyclization to the desired product of Formula I. The mixture is generally heated in the absence of solvent at 100° to 150° C.

An alternative, one-step process in accordance with the present invention is illustrated in general terms as follows in Procedure B:

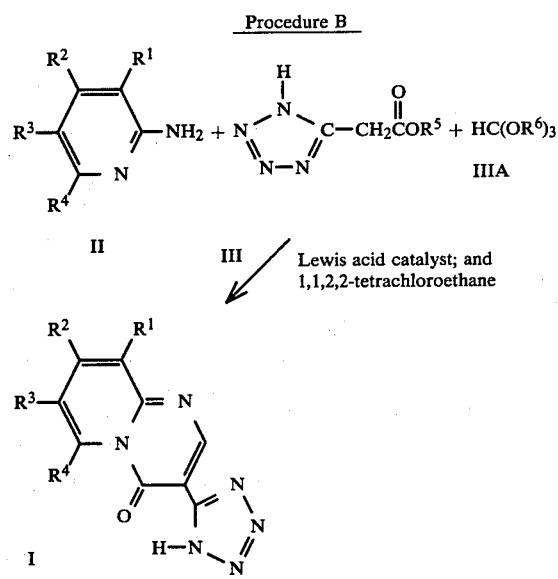

Procedure B wherein $R^1$, $R^2$, $R^3$, $R^4$, $R^5$ and $R^6$ are as defined previously.

In Procedure B, reaction of a 2-aminopyridine of Formula II, an alkyl tetrazol-5-ylacetate of Formula III, and a trialkyl orthoformate ester of Formula IIIA in the presence of a Lewis acid catalyst and the cyclization of the resulting intermediate to form the compound of Formula I occur sequentially in a one-step process when the indicated 1,1,2,2-tetrachloroethane is employed as the solvent. The reaction mixture is generally heated at about 100° to 150° C., 130° C. being the preferred temperature. Suitable trialkyl orthoformate esters and Lewis acid catalysts include those discussed above in connection with Procedure A.

The final products of the processes of the invention are readily isolated and purified using state of the art methods such as extraction, filtration, recrystallization and chromatographic techniques.

The following examples are provided for the purpose of further illustrating the invention but are not intended to limit the scope thereof in any way.

EXAMPLE 1

Synthesis of
3-(1H-Tetrazol-5-yl)-4H-pyrido[1,2-a]pyrimidine-4-one

A mixture of 0.94 g (10 mmole) of 2-aminopyridine, 1.56 g (10.0 mmole) of ethyl tetrazol-5-ylacetate, 2.00 g (13.5 mmole) of triethyl orthoformate and 0.2 g (1.5 mmole) of aluminum chloride was heated at 110° to 120° C. in an open flask for 30 minutes. The mixture was cooled and triturated with aqueous methanol. The solid was separated by filtration and washed sequentially with water and a small amount of methanol to provide 2.32 g (89%) of pale yellow solid ethyl 2-[N-(2-pyridyl)amino]-1-(1H-tetrazol-5-yl)acrylate. The structural assignment was confirmed by infrared and nuclear magnetic resonance spectral analyses.

A stirred mixture of 12 g of polyphosphoric acid and 3.00 g (11.5 mmole) of the ethyl 2-[N-(2-pyridyl)amino]-1-(1H-tetrazol-5-yl)acrylate prepared above was heated to 130° C. over 30 minutes and maintained at that temperature for an additional 30 minutes. After cooling, 100 ml of water was added to the thick mixture. The mixture was neutralized with concentrated ammonium hydroxide and the resulting solid was separated by filtration and washed with water. The product was 1.74 g (71%) of 3-(1H-tetrazol-5-yl)-4H-pyrido[1,2-a]pyrimidin-4-one. The structural assignment was confirmed by infrared spectral analysis. Further purification was carried out by suspending the product in 40 ml of hot N,N-dimethylformamide, cooling the mixture and filtering the solid. The solid was then resuspended in 70 ml of hot water. The mixture was filtered while hot, and the solid was washed sequentially with water and methanol and then dried to provide an off-white-colored solid.

EXAMPLE 2

Alternative Synthesis of
3-(1H-Tetrazol-5-yl)-4H-pyrido[1,2-a]pyrimidine-4-one

A mixture of 0.94 g (10.0 mmole) of 2-aminopyridine, 1.56 g (10.0 mmole) of ethyl tetrazol-5-ylacetate, 1.65 g (11.1 mmole) of triethyl orthoformate and 0.3 g (2.2 mmole) of aluminum chloride in 50 ml of 1,1,2,2-tetrachloroethane was heated at 120° C. under a nitrogen atmosphere for 3 days. The mixture was cooled, diluted to 200 ml with diethyl ether and filtered. The solid obtained was suspended in 100 ml of 1:1 methanol-water. The solid was then separated by filtration and washed with methanol to provide 1.39 g (65%) of off-white-colored solid 3-(1H-tetrazol-5-yl)-4H-pyrido[1,2-a]pyrimidine-4-one. The infrared spectrum of the product confirmed the structural assignment.

EXAMPLES 3-9

The following Table (I) described several compounds of Formula I which may be made by following Procedure A of the invention and employing ethyl tetrazol-5-yl-acetate as the alkyl tetrazol-5-ylacetate of Formula III. Table (I) indicates which known starting materials may be used to prepare compounds of Formula I. The novel intermediates of Formula IV which are formed in Procedure A are also described in Table (I). The compounds of Formula I described below may also be prepared from the indicated starting material by following Procedure B of the invention. When Procedure B is followed the intermediate of Formula IV is not isolated.

TABLE I
| Example | Starting Material of Formula II | Intermediate of Formula IV | Final Product of Formula I |
|---|---|---|---|
| 3 |  (2-amino-5-bromopyridine) | 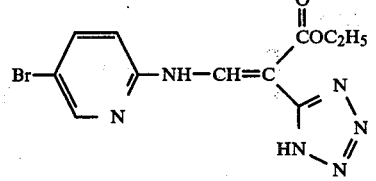 | 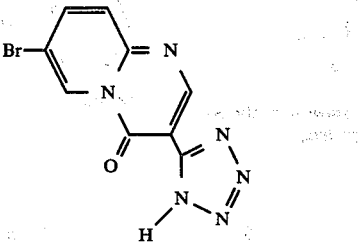 |
| 4 | 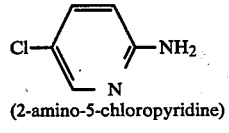 (2-amino-5-chloropyridine) | 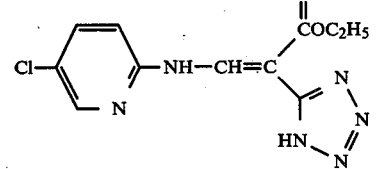 | 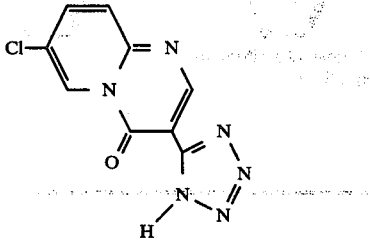 |
| 5 | 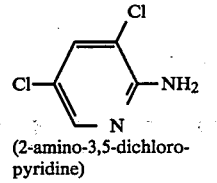 (2-amino-3,5-dichloropyridine) | 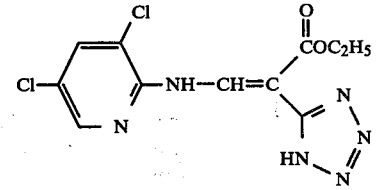 | 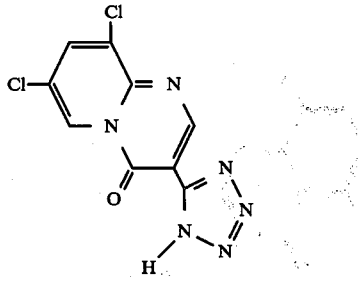 |
| 6 | 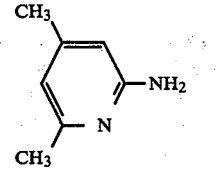 (2-amino-4,6-dimethylpyridine) | 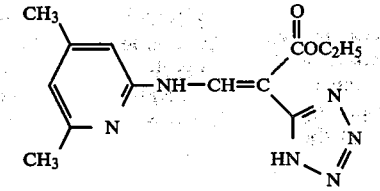 | 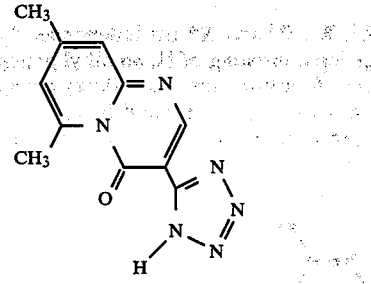 |
| 7 | 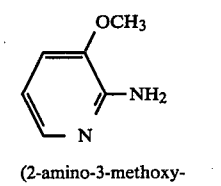 (2-amino-3-methoxypyridine) | 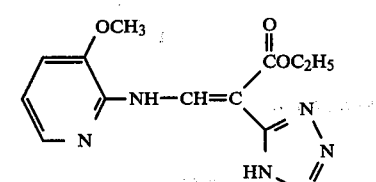 | 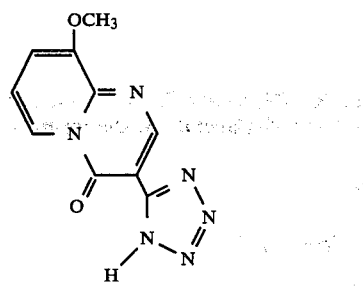 |

TABLE I-continued

| Example | Starting Material of Formula II | Intermediate of Formula IV | Final Product of Formula I |
|---|---|---|---|
| 8 | 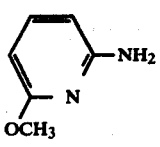<br>(2-amino-6-methoxy-pyridine) | 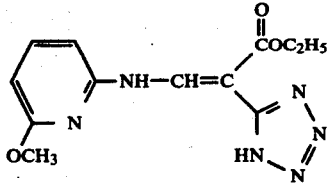 | 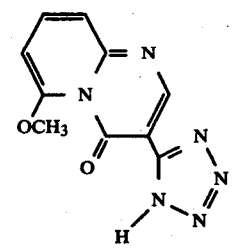 |
| 9 | 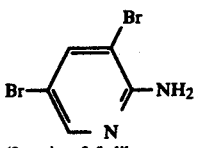<br>(2-amino-3,5-dibromo-pyridine) | 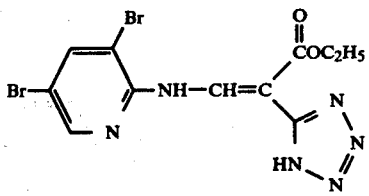 | 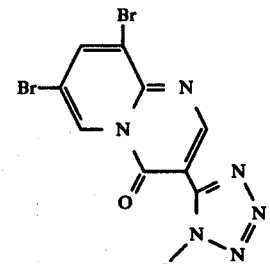 |

What is claimed is:

1. A process for the preparation of a compound of formula

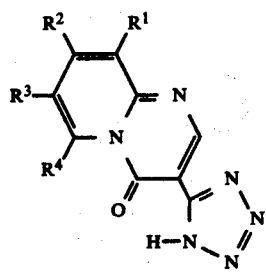

wherein $R^1$, $R^2$, $R^3$ and $R^4$ are independently selected from the group consisting of H, an alkyl group containing 1 to about 4 carbon atoms, an alkoxy group containing 1 to about 4 carbon atoms and halogen, comprising (1) reacting together a 2-aminopyridine amine of the formula

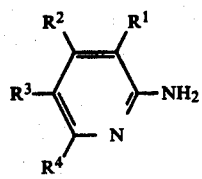

wherein $R^1$, $R^2$, $R^3$ and $R^4$ are defined as above, an alkyl tetrazol-5-ylacetate of the formula

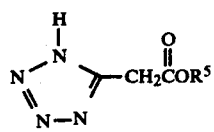

wherein $R^5$ is an alkyl group containing 1 to about 4 carbon atoms, and a trialkyl orthoformate of the formula

HC(OR⁶)₃ wherein $R^6$ is an alkyl group containing 1 to about 4 carbon atoms in the presence of a Lewis acid to provide a 2-(N-pyridyl)amino-1-(1H-tetrazol-5-yl)acrylate ester; and (2) condensing the 2-(N-pyridyl)amino-1-(1H-tetrazol-5-yl)acrylate ester in the presence of polyphosphoric acid to provide said compound.

2. A process for the preparation of a compound of the formula

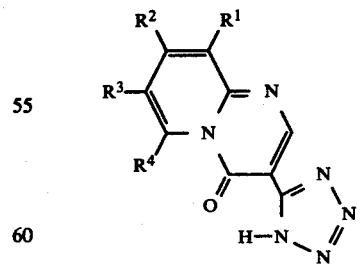

wherein $R^1$, $R^2$, $R^3$ and $R^4$ are independently selected from the group consisting of H, an alkyl group containing 1 to about 4 carbon atoms, an alkoxy group containing 1 to about 4 carbon atoms and halogen;

comprising reacting together a 2-aminopyridine of the formula

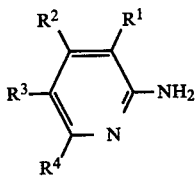

wherein $R^1$, $R^2$, $R^3$ and $R^4$ are defined as above, an alkyl tetrazol-5-ylacetate of the formula

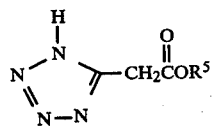

wherein $R^5$ is an alkyl group containing 1 to about 4 carbon atoms, and a trialkyl orthoformate of the formula

wherein $R^6$ is an alkyl group containing 1 to about 4 carbon atoms in the presence of a Lewis acid and 1,1,2,2-tetrachloroethane.

3. A process in accordance with claim 1 or 2, wherein said trialkyl orthoformate is selected from the group consisting of trimethyl orthoformate and triethyl orthoformate.

4. A process in accordance with claim 1 or 2, wherein said Lewis acid is aluminum trichloride.

5. A compound of the formula

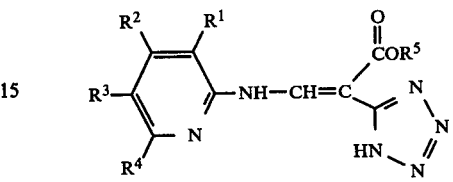

wherein $R^1$, $R^2$, $R^3$ and $R^4$ are independently selected from the group consisting of H, an alkyl group containing 1 to about 4 carbon atoms, an alkoxy group containing 1 to about 4 carbon atoms and halogen, and $R^5$ is an alkyl group containing 1 to about 4 carbon atoms.

* * * * *